US008532430B2

United States Patent
Hazard

(10) Patent No.: US 8,532,430 B2
(45) Date of Patent: Sep. 10, 2013

(54) METHODS FOR REDUCING MOTION ARTIFACTS IN SHEAR WAVE IMAGES

(75) Inventor: Christopher Robert Hazard, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 212 days.

(21) Appl. No.: 13/192,569

(22) Filed: Jul. 28, 2011

(65) Prior Publication Data

US 2013/0028536 A1    Jan. 31, 2013

(51) Int. Cl.
  *G06K 9/00* (2006.01)
  *G06K 9/40* (2006.01)
  *G06K 9/32* (2006.01)
  *A61B 8/00* (2006.01)

(52) U.S. Cl.
  USPC ........... 382/275; 382/103; 382/128; 382/260; 382/300; 600/437; 600/443

(58) Field of Classification Search
  USPC ......... 382/128–132, 260–266, 275; 600/437, 600/438, 443, 447, 454
  See application file for complete search history.

(56) References Cited

U.S. PATENT DOCUMENTS

| 4,422,165 | A | 12/1983 | Thomas et al. | |
|---|---|---|---|---|
| 4,446,541 | A | 5/1984 | Cowles | |
| 6,048,316 | A | 4/2000 | Zhao et al. | |
| 7,374,538 | B2 | 5/2008 | Nightingale et al. | |
| 8,118,744 | B2 * | 2/2012 | Palmeri et al. | 600/437 |
| 8,306,293 | B2 * | 11/2012 | Walker et al. | 382/128 |
| 2005/0215899 | A1 * | 9/2005 | Trahey et al. | 600/439 |
| 2007/0034014 | A1 | 2/2007 | Armstrong et al. | |
| 2008/0249408 | A1 | 10/2008 | Palmeri et al. | |
| 2010/0069751 | A1 * | 3/2010 | Hazard et al. | 600/438 |
| 2010/0138163 | A1 * | 6/2010 | Gallippi et al. | 702/19 |
| 2011/0063950 | A1 * | 3/2011 | Greenleaf et al. | 367/87 |
| 2012/0065507 | A1 * | 3/2012 | Brunke | 600/442 |
| 2012/0089019 | A1 * | 4/2012 | Fan | 600/437 |
| 2012/0123492 | A1 * | 5/2012 | Hunt et al. | 607/7 |
| 2012/0158323 | A1 | 6/2012 | Hazard et al. | |

OTHER PUBLICATIONS

Dahl et al, A Parallel Tracking Method for Acoustic Radiation Force Impulse Imaging, IEEE Trans Ultrason Ferroelectr Freq Control. Feb. 2007; 54(2): 301-312.*

(Continued)

*Primary Examiner* — Andrae S Allison
(74) *Attorney, Agent, or Firm* — Scott J. Asmus

(57) ABSTRACT

Methods and non-transitory computer readable media that store executable instructions to perform a method for reducing motion artifacts in shear wave measurements are presented. Accordingly, reference pulses are delivered to a common motion tracking location (CMTL) and a plurality of target locations in a region of interest (ROI) to detect corresponding initial positions. Further, a shear wave is generated and tracked in the ROI using tracking pulses delivered to the CMTL and the plurality of target locations for determining corresponding displacements. Additionally, an average displacement of the CMTL is computed. Further, a motion corrected displacement for a target location in the plurality of target locations is estimated based on a displacement of the target location at a particular time, a corresponding displacement of the CMTL measured proximate in time to the measurement of the displacement of the target location and the average displacement of the CMTL.

20 Claims, 9 Drawing Sheets

(56) References Cited

OTHER PUBLICATIONS

Urban, M.W.; Shigao Chen; Greenleaf, J.F., "Error in estimates of tissue material properties from shear wave dispersion ultrasound vibrometry," Ultrasonics, Ferroelectrics and Frequency Control, IEEE Transactions on , vol. 56, no. 4, pp. 748,758, Apr. 2009.*

Q. C. C. Chan et al.; "Shear waves induced by moving needle in MR Elastography"; Proceedings of the 26th Annual International Conference of the IEEE EMBS San Francisco, CA, USA • Sep. 1-5, 2004; 0-7803-8439-3/04/$20.00 © 2004 IEEE; pp. 1022-1024.

Mostafa Fatemi et al.; "Imaging Elastic Properties of Biological Tissues by Low-Frequency Harmonic Vibration"; Proceedings of the IEEE, vol. 91, No. 10, Oct. 2003; 0018-9219/03$17.00 © 2003 IEEE; pp. 1503-1519.

Anthony J. Romano et al.; "Evaluation of a Material Parameter Extraction Algorithm Using MRI-Based Displacement Measurements"; IEEE transactions on ultrasonics, ferroelectrics, and frequency control, vol. 47, No. 6, Nov. 2000; pp. 1575-1581.

* cited by examiner

METHODS FOR REDUCING MOTION ARTIFACTS IN SHEAR WAVE IMAGES

STATEMENT OF GOVERNMENT INTEREST

This invention was made with government support R01 AG029804 awarded by National Institutes of Health. The government has certain rights in the invention.

BACKGROUND

Embodiments of the disclosure relate to diagnostic imaging, and more particularly to methods for reducing motion artifacts in shear wave measurements.

Medical diagnostic ultrasound is an imaging modality that employs ultrasound waves to probe the acoustic properties of biological tissues and produce corresponding images. Particularly, diagnostic ultrasound systems are used to visualize muscles, tendons and other internal organs to assess their size, structure and any pathological lesions using near real-time tomographic images. Further, diagnostic ultrasound also finds use in therapeutics where an ultrasound probe is used to guide interventional procedures such as biopsies.

To that end, conventional ultrasound devices include a plurality of transducer elements that convert electrical energy into mechanical energy for transmission, and mechanical energy back into electrical signals on reception. The ultrasound devices then process and transform the received electrical signals into a digital image of a target region, such as biological tissues, in near real time for facilitating further evaluation and therapy.

Recent ultrasound imaging techniques employ acoustically generated shear waves to determine the mechanical properties of biological tissues. Particularly, some of these techniques track shear wave induced displacements through a region of interest (ROI) to determine tissue mechanical properties such as shear speed and shear elastic modulus. To that end, the ultrasound devices generate shear waves in a target ROI in a corresponding phantom or actual biological tissues, for example, by delivering one or more pushing pulses. The generated shear waves cause time varying displacements while traveling from the point of generation to multiple locations along the target tissues. The ultrasound device may detect these displacements, for example, using standard Doppler tracking pulses. Particularly, tracking the shear wave induced displacements as a function of time at the multiple locations allows for shear velocity estimation, which in turn, aids in estimating one or more mechanical properties of the target tissues.

Characterization of tissue mechanical properties such as shear stiffness using shear velocity estimation has important medical applications as these properties are closely linked to tissue state with respect to pathology. Typically, at least a portion of a tissue may become stiffer than surrounding tissues indicating an onset or presence of a disease or condition such as cancer, tumor, fibrosis or steatosis.

Conventional shear velocity imaging techniques, however, suffer from probe and patient motion artifacts such as image blur, decorrelation, and groupings or stripes along the axial direction. These artifacts are more prevalent when a large ROI is generated from multiple acquisitions taken at different instants of time. The background motion will be different during the multiple acquisitions, which in turn, leads to the appearance of the striped artifacts in the shear wave displacement images.

In particular, movement of the ultrasound probe relative to the patient or internal motion such as respiration, cardiac motion, tremors and/or vibrations during the course of the multiple acquisitions can also corrupt the measured displacements. The patient's cardiac motion, for example, may cause an axial displacement of ultrasound transducers on the order of about 1.5 mm to about 6 mm during systolic and diastolic phases of the cardiac cycle. Similarly, other movements such as respiration may cause displacements of varying orders resulting in artifacts in the shear wave displacement images. Attempts to prevent appearance of motion artifacts due to background and/or patient motion using mitigating approaches such as specifically designed motion filters are often complex and require additional processing time and expense.

Thus, it is desirable to develop effective methods and systems for reducing appearance of motion artifacts during shear wave imaging. Particularly, there is a need for methods and systems that prevent, or at least substantially reduce the motion artifacts when imaging biological tissues using multiple acquisitions.

BRIEF DESCRIPTION

Certain aspects of the present technique are drawn to exemplary methods for reducing motion artifacts in shear wave measurements. The methods include delivering one or more reference pulses to a common motion tracking location and to a plurality of target locations in a region of interest of a subject to detect initial positions of the common motion tracking location and the plurality of target locations. Further, a shear wave is generated in the region of interest. Additionally, one or more tracking pulses are delivered to the common motion tracking location and to the plurality of target locations for determining corresponding displacements. The methods compute an average value of displacement of the common motion tracking location. Further, the methods estimate a motion corrected displacement for a target location in the plurality of target locations based on a displacement of the target location at a particular time, the corresponding displacement of the common tracking location measured proximate in time to the measurement of the displacement of the target location and the average value of displacement of the common motion tracking location.

Another aspect of the present technique includes further methods for reducing motion artifacts in shear wave measurements. To that end, the methods deliver at least two groups of shear wave scan sequences. Each of these groups comprises delivering one or more reference pulses to a first set of target locations in a region of interest of a subject to detect corresponding initial positions, where at least one of the first set of target locations is common to a second set of target locations. Further, a shear wave is generated in the region of interest. One or more tracking pulses are then delivered to the first set of target locations for determining corresponding displacements. Further, displacements for the first set of target locations are computed based on measurements captured using the one or more reference pulses and the one or more tracking pulses delivered to the corresponding target locations in the first set of target locations. Particularly, for each group of shear wave sequences, the determined displacements for the first set of target locations and the second set of target locations is interpolated to a common time. Further, a difference between the interpolated displacement of a target location in the first set of target locations and the interpolated displacement of another target location in the first set of target locations is computed. Additionally, the methods include estimating a seed value using the measured and interpolated displacements from the target location in the first set of target locations. Motion corrected displacements for other target locations in the first set of target locations are estimated based on the estimated seed value and the computed difference between interpolated displacement of the target location and the interpolated displacement of another target location in the first set of target locations. Additionally, motion corrected displacements for the second set of target locations are estimated using the computed difference and the motion corrected displacements estimated for target locations in the first set of target locations that are common to the second set of target locations.

Furthermore, non-transitory computer readable media that store instructions executable by one or more processors to perform a method for reducing motion artifacts in shear wave measurements using the exemplary methods described herein are also disclosed.

One technical effect of the methods and systems of the present disclosure is for reducing appearance of motion artifacts during shear wave imaging. In particular, a technical effect prevents or at least substantially reduces the motion artifacts such as image blur, decorrelation, and/or axial stripes when imaging biological tissues using multiline acquisitions.

DRAWINGS

These and other features, aspects, and advantages of the present technique will become better understood when the following detailed description is read with reference to the accompanying drawings in which like characters represent like parts throughout the drawings, wherein.

Figure 6:
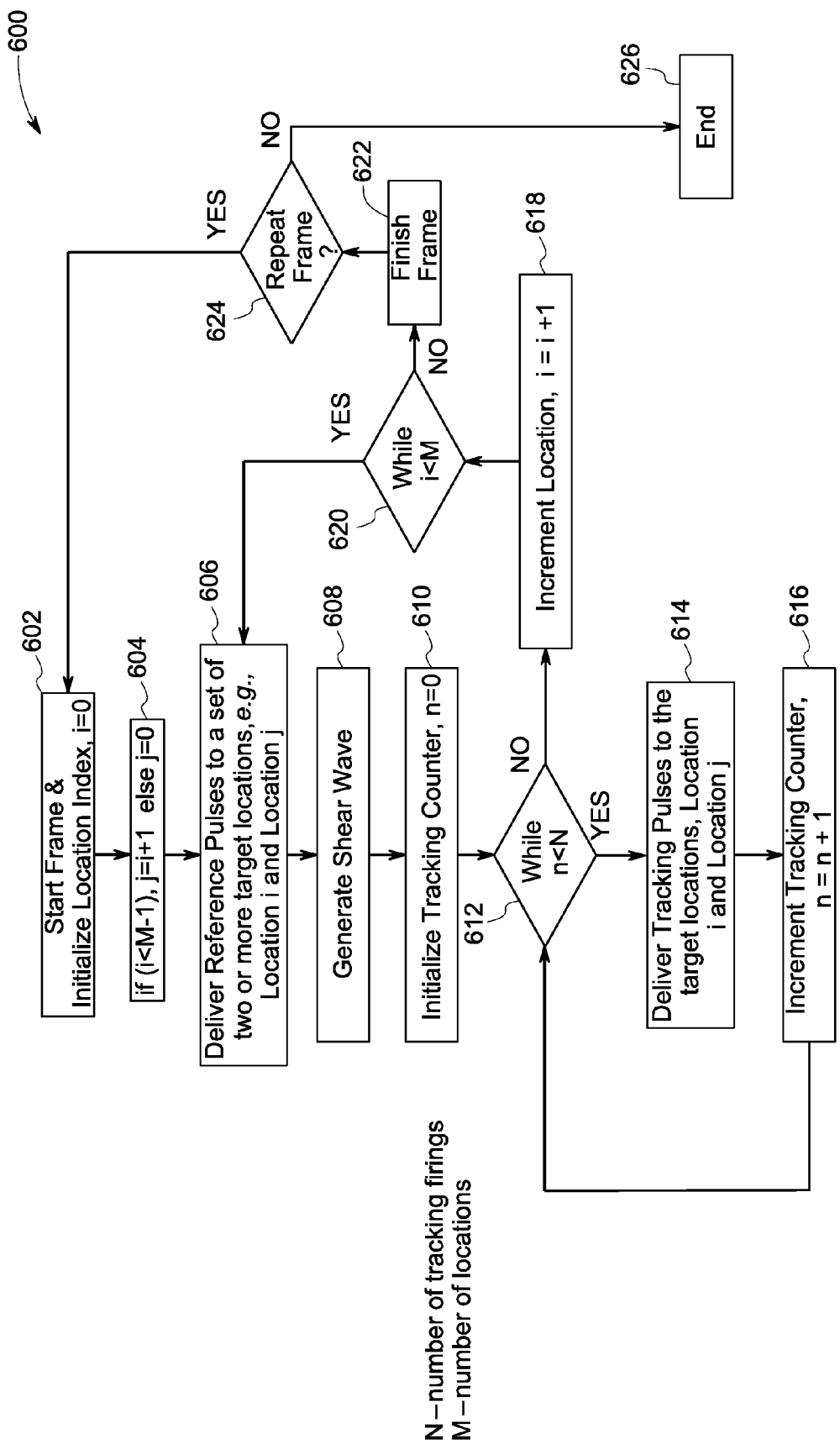
FIG. 6 is a flow diagram illustrating an exemplary method for acquiring shear wave displacements at a plurality of target locations using pairs of tracking locations, in accordance with aspects of the present technique.
Figure 8:
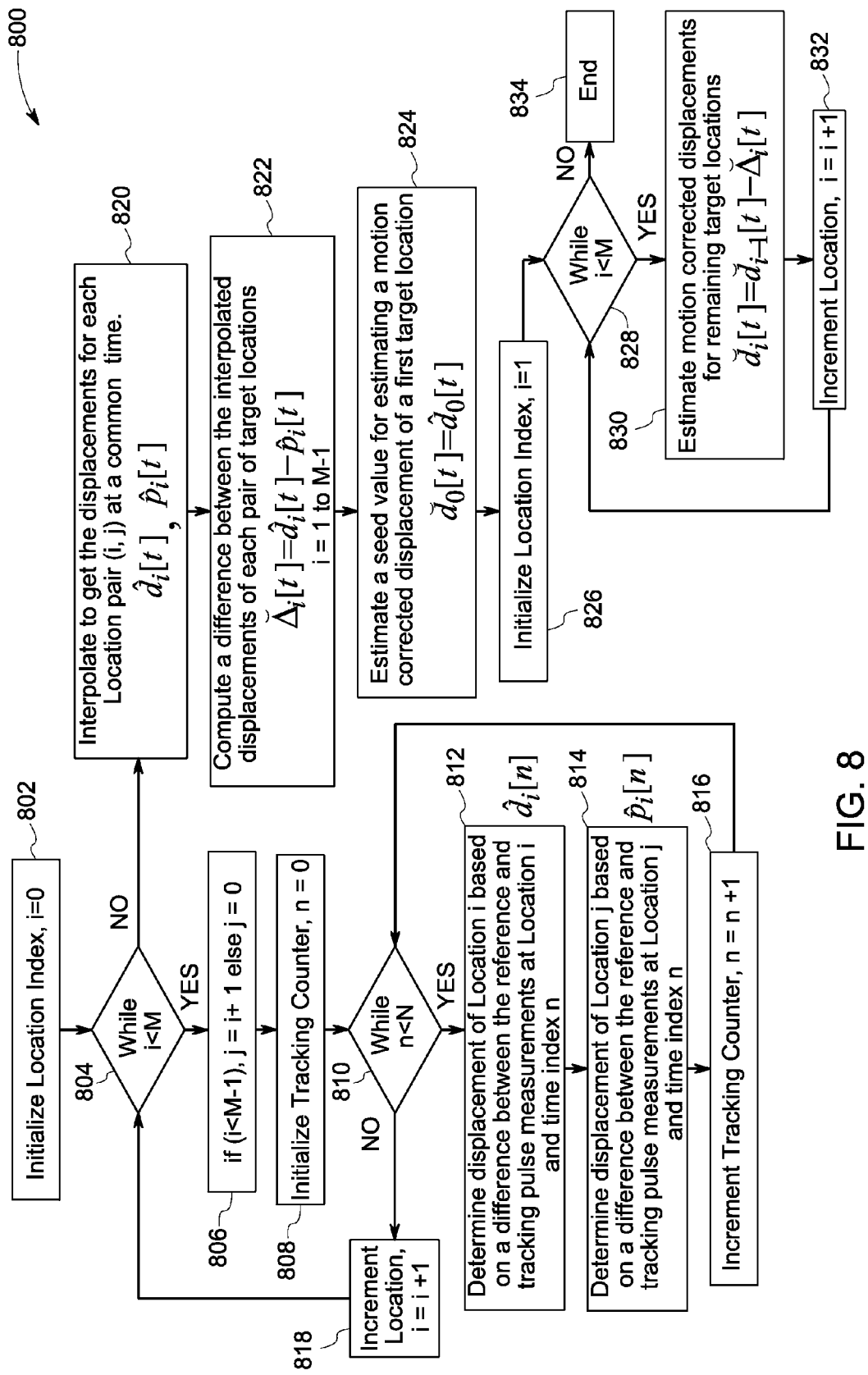
Figure 9:
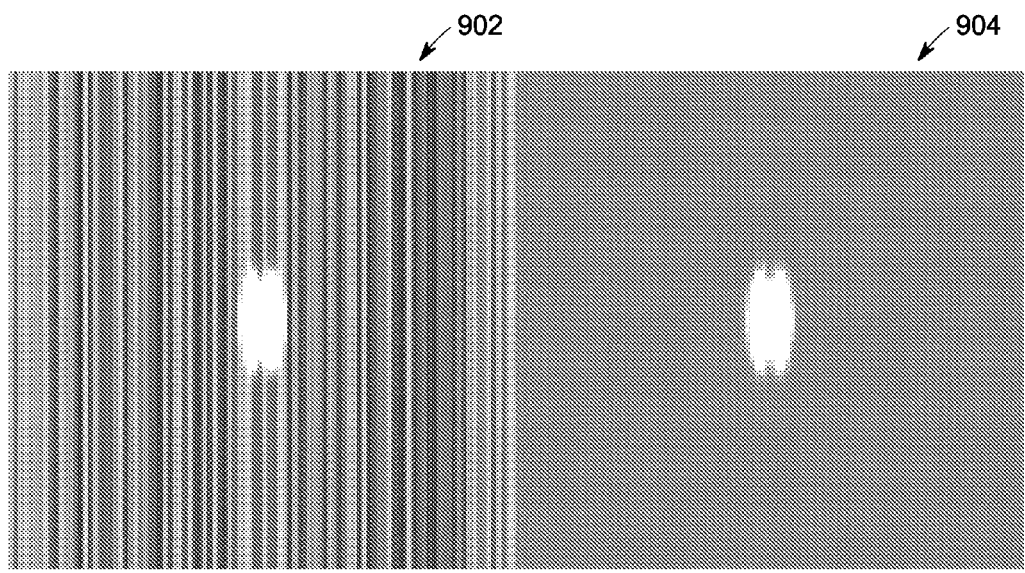

FIG. 8 is a flow diagram illustrating an exemplary method for processing the shear wave displacements acquired using the method of FIG. 6 for estimating motion corrected shear wave displacements at the plurality of target locations using pairs of tracking locations, in accordance with aspects of the present technique; and FIG. 9 is an exemplary illustration depicting a comparison of a raw image including motion artifacts and a corresponding motion corrected image generated in accordance with aspects of the present technique.

DETAILED DESCRIPTION

The following description presents systems and methods for reducing appearance of motion artifacts in shear wave displacement images. Particularly, certain embodiments illustrated herein describe the systems and the methods that efficiently mitigate the errors in the measured displacement values of one or more target locations in the ROI of a subject by evaluating the measured values with reference to the displacements measured at one or more tracking locations. The systems and methods use the evaluation for substantially improving the estimation of motion-corrected displacement values of the target locations, which in turn, reduces motion artifacts in the corresponding reconstructed images.

Although the following description includes embodiments relating to ultrasound imaging, the various embodiments may also be implemented in connection with other types of medical imaging systems, such as magnetic resonance imaging (MRI) systems, computed-tomography (CT) systems, and systems that monitor targeted drug and gene delivery. Particularly, the systems and methods described herein, for example, find use in improving detection of cancerous lesions in breast, thyroid, liver, or other organs of a human subject. The present systems and methods may also be used to more accurately diagnose and stage liver fibrosis and to help monitor therapies including, high-intensity focused ultrasound (HIFU), radiofrequency ablation (RFA), and brachytherapy using motion-corrected shear wave measurements.

In certain embodiments, the present systems and methods can also be used for non-medical purposes, such as for non-destructive testing of subject elastic materials such as plastics and aerospace composites that may be suitable for ultrasound imaging and airport screening. An exemplary environment that is suitable for practicing various implementations of the present system is described in the following sections with reference to FIG. 1.

Figure 1:
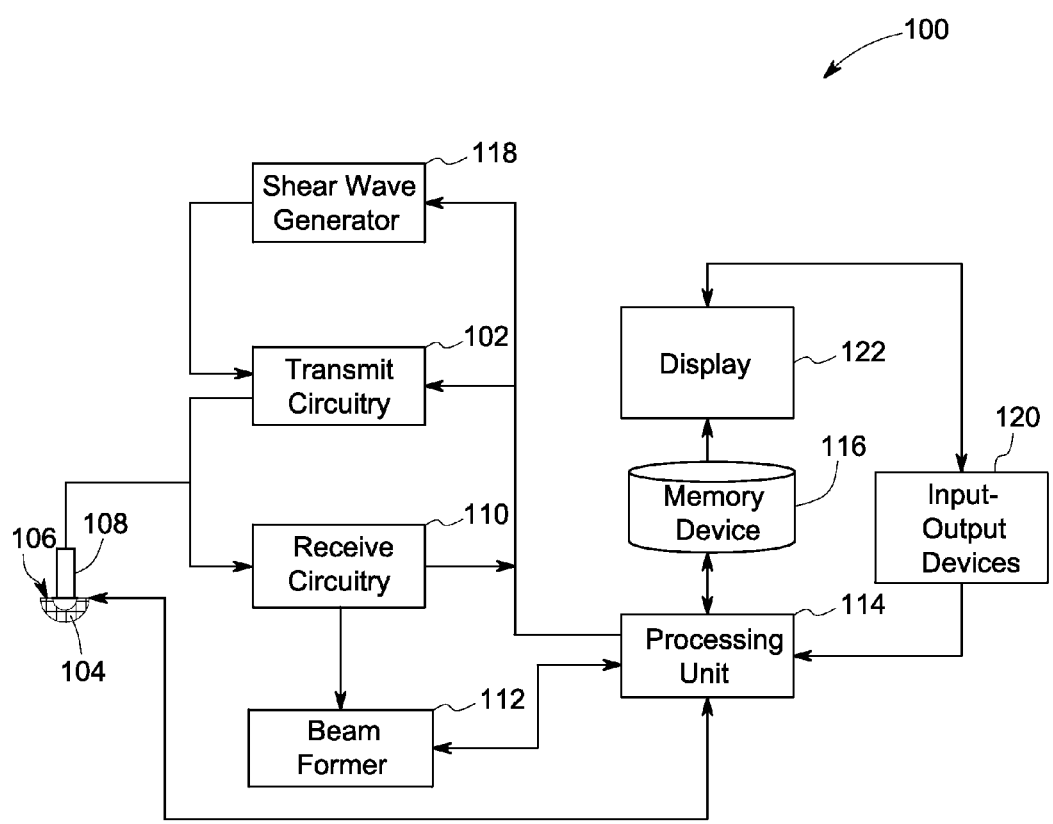
FIG. 1 is a schematic representation of an exemplary ultrasound imaging system, in accordance with aspects of the present system.

FIG. 1 illustrates an ultrasound system 100, for example, for use in therapy, in imaging one or more target locations and other suitable purposes that may employ one or more ultrasound pulses. The present embodiment describes the use of the ultrasound system 100 for imaging one or more target locations in biological tissues of interest. By way of example, the target locations may include biological tissues such as cardiac tissues, liver tissues, breast tissues, prostate tissues, thyroid tissues, lymph nodes, vascular structures and/or other objects suitable for ultrasound imaging. Further, the ultrasound pulses may include, for example, one or more reference pulses, one or more pushing pulses and/or one or more tracking pulses.

As used herein, the term "reference pulse" refers to an ultrasonic beam fired at a time when there is little expected motion or a known amount of motion. The reference pulse is typically fired prior to a pushing pulse, or long after a push at an instant of time when the tissue is considered to have returned to a resting or equilibrium position. Particularly, the reference pulse is fired to detect an initial or a reference position of the target locations. The term "pushing pulse" refers to a high energy ultrasonic beam used to displace the target tissues. Typically, the pushing pulse has a higher transmitting energy than the reference pulse. Further, the term "tracking pulse" describes an ultrasound beam similar to a reference pulse used to detect the position of the target locations at a particular instant of time. By way of example, the tracking pulse may be delivered shortly after the delivery of a pushing pulse to determine a displaced position of the target locations.

Accordingly, in certain embodiments, the system 100 includes transmit circuitry 102 that generates a pulsed waveform to drive an array 106 of transducer elements 104, for example piezoelectric crystals within a transducer probe 108, to emit ultrasonic pulses into a body or volume of a subject (not shown). At least a portion of the ultrasonic pulses backscatter from the target locations, for example, adipose tissue, muscular tissue, connective tissue, blood cells, veins or objects within the body such as a catheter or needle to produce echoes that return to the transducer array 106 and are received by a receive circuitry 110 for further processing.

To that end, in one embodiment, the receive circuitry 110 is coupled to a beamformer 112 that processes the received echoes and outputs corresponding radio frequency (RF) signals. The RF signals are then provided to a processing unit 114 that processes the RF signals according to a plurality of selectable ultrasound modalities in near real time and/or offline mode. Accordingly, the processing unit 114 includes devices such as one or more general-purpose or application-specific processors, digital signal processors, microcomputers, microcontrollers, Application Specific Integrated Circuits (ASICs), Field Programmable Gate Arrays (FPGA) or other suitable devices in communication with other components of the system 100.

Furthermore, the processing unit 114 provides control and timing signals for controlling the delivery sequence of the different pulses, frequency of delivering the tracking pulses and the pushing pulses, a time delay between two different pulses, beam intensity and/or other imaging system parameters. Particularly, in accordance with aspects of the present technique, the processing unit 114 provides appropriate timing and control signals to the transducer probe 108 and/or the transmit circuitry 102 for generating a shear wave in a target region of a biological tissue.

In certain embodiments, the processing unit 114 stores the delivery sequence, frequency, time delay, beam intensity and/or imaging system parameters along with other operational data in a memory device 116 for further processing. To that end, the memory device 116 includes storage devices such as a random access memory, a read only memory, a disc drive, solid-state memory device and/or a flash memory. Alternatively, the processing unit 114 communicates the determined values to a shear wave generator 118 for generating a shear wave in a region of interest (ROI) of the target tissues. To that end, the shear wave generator 118, for example, includes one or more amplifiers, analog-to digital converters, digital-to-analog converters, filters, a memory and/or a PCI bus interface (not shown). Although, FIG. 1 illustrates the shear wave generator 118 as an independent entity, in certain embodiments, the shear wave generator 118 may be implemented as part of the processing unit 114 or the transmit circuitry 102.

In one embodiment, the shear wave generator 118 controls the probe 108 or, more particularly, the transducer elements 104 to direct one or more groups of pulse sequences toward the target tissues to generate the shear wave. Alternatively, the shear-wave-generating module 118 controls another device (not shown) capable of generating shear waves, such as, a therapy transducer, a mechanical actuator, electromagnetic means or an audio device to generate the shear wave in the target tissues. The processing unit 114 then tracks the displacements in the ROI of the target tissues caused by the shear wave to determine corresponding tissue characteristics.

Accordingly, in certain embodiments, the processing unit 114 is further coupled to one or more user input/output devices 120 such as a keyboard, touchscreen, microphone, mouse, buttons and/or switches for receiving commands and inputs from an operator. In one example the processing unit 114 processes the RF signal data and prepares frames based on user-selected ROI and information for display on a display device 122, local or remote, communicatively coupled to the processing unit 114 and/or the input output devices 120.

Particularly, the processing unit 114 evaluates the acquired ultrasound information and displays corresponding output patient data including diagnostic and therapeutic ultrasound images for review, diagnosis, analysis and treatment. In another example, the processing unit 114 stores the frames of the ROI for later review and analysis or communicates the frames to another location for further review. Further, in one embodiment, the display device 122 includes a graphical user interface (GUI) for providing a user with configurable options for imaging the target locations. By way of example, the configurable options may include a selectable ROI, a delay profile, a designated pulse sequence, a desired pulse repetition frequency and/or other suitable imaging system settings to generate shear wave in the desired ROI.

Figure 2A:
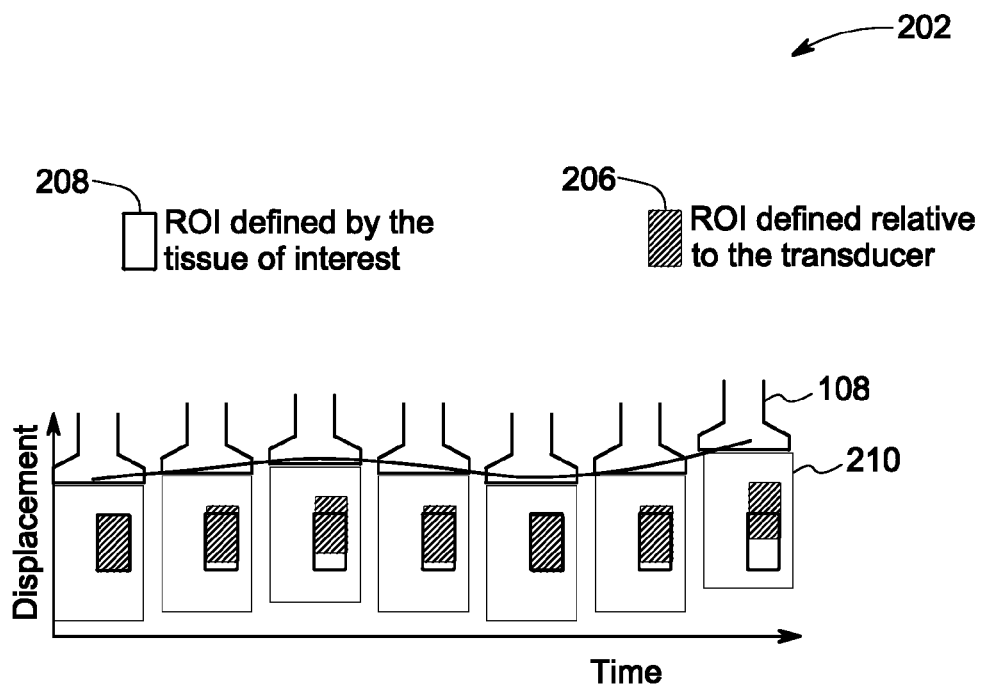
FIG. 2a is a schematic representation of examples of erroneous estimation of an ROI caused by probe motion.
Figure 2B:
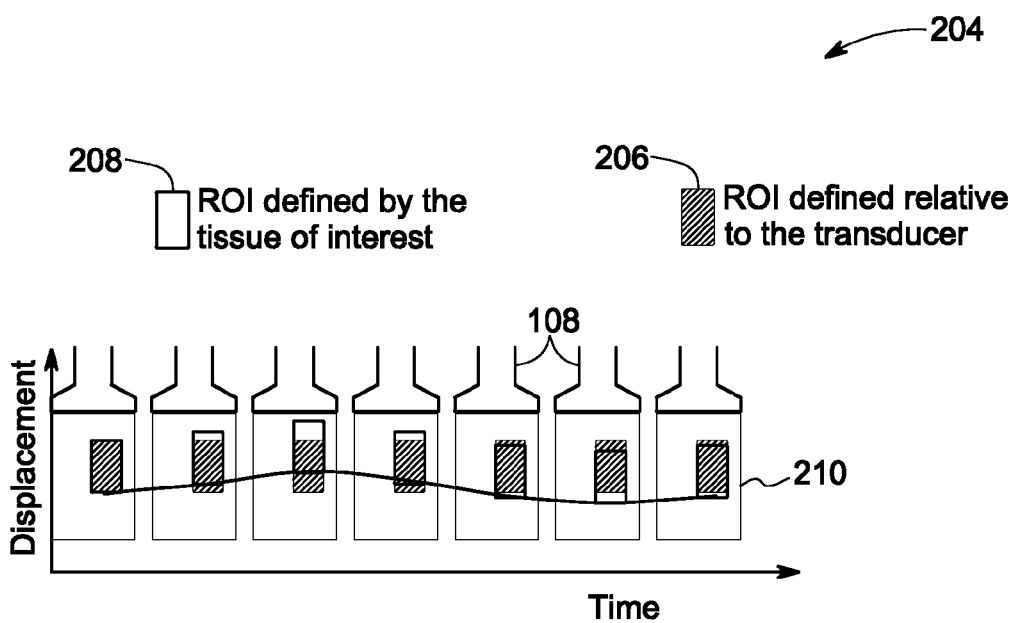
FIG. 2b is a schematic representation of examples of erroneous estimation of an ROI caused by patient motion.

Conventional ultrasound systems employ multiple shear wave excitations to build a large ROI. Any background motion present during data acquisition, however, will be different for different excitations, thus corrupting the displacement measurements and leading to motion artifacts in the ROI image. FIGS. 2a and 2b illustrate schematic representations 202 and 204 depicting examples of erroneous estimation of an ROI caused by probe motion and patient motion, respectively. Particularly, FIGS. 2a and 2b depict how the probe or patient motion that is not associated with the generated shear wave can cause, for example, an axial translation for the entire ROI, thus corrupting the estimated shear wave displacements.

To that end, in FIGS. 2a and 2b, element 206 is representative of the ROI defined relative to the transducer probe 108, whereas element 208 is representative of the ROI defined by a tissue of interest 210. As evident from the depictions of the tissue ROI 208 and the probe ROI 206 in FIGS. 2a and 2b, motion of the ultrasound probe 108 and/or patient motion such as cardiac and respiratory motion causes the tissue ROI 208 to move axially/vertically, laterally and/or out of plane in relation to the probe ROI 206.

Occurrence of such background motion during the tracking firings for a particular target location corrupts shear wave displacements estimated for the target location. The corrupted shear wave measurements, in turn, result in the appearance of motion artifacts, such as striped noise patterns, in the shear wave displacement images leading to erroneous diagnosis and/or prognosis. Accordingly, the ultrasound system 100 employs specific acquisition and processing steps to mitigate the corrupting effects of common background motion experienced during ultrasound imaging. Exemplary methods describing the specific acquisition and processing steps for reducing motion artifacts in shear wave measurements will be described in greater detail with reference to FIGS. 3-8.

Figure 3:
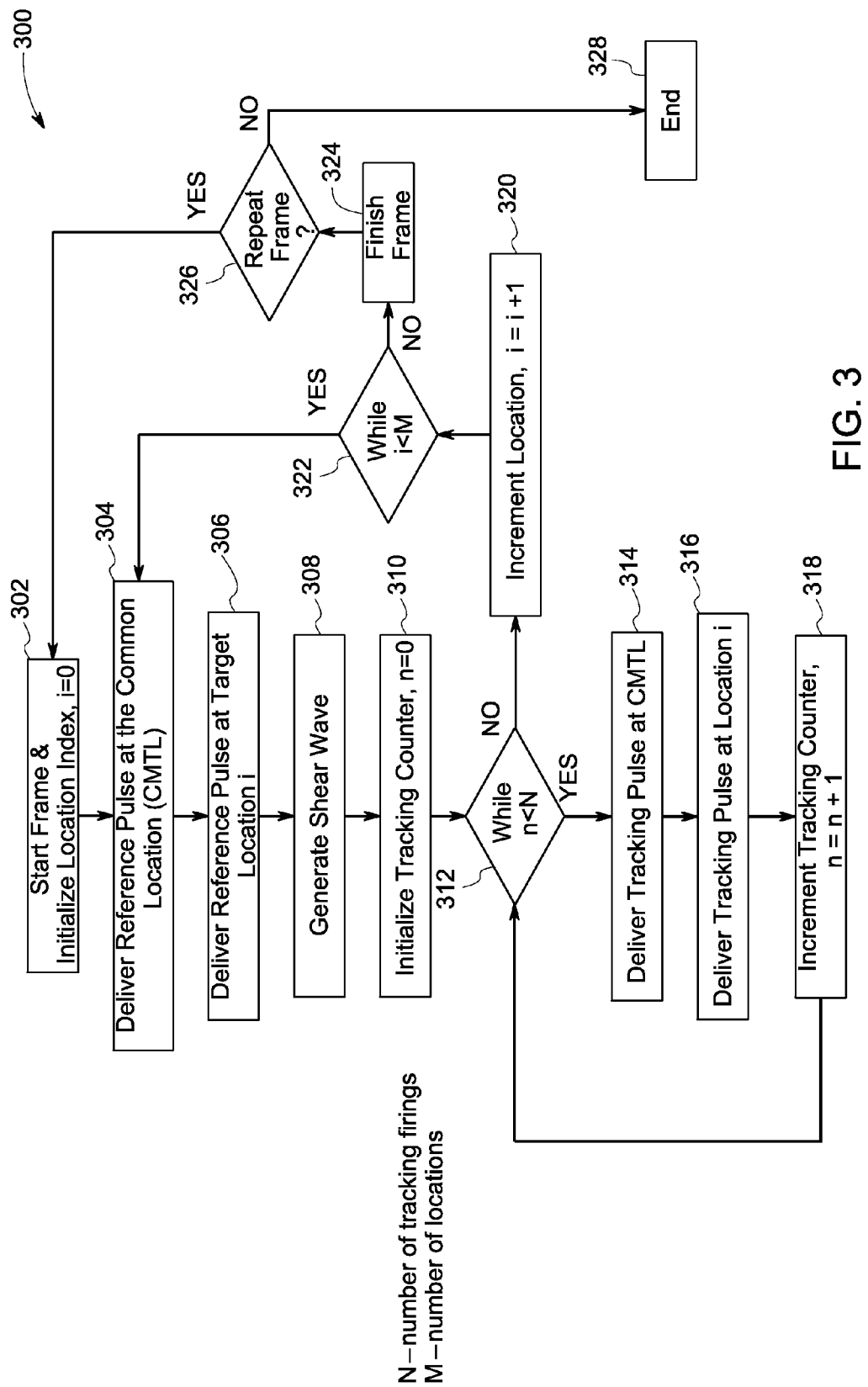
FIG. 3 is a flow diagram illustrating an exemplary method for acquiring shear wave displacements at a plurality of target locations using a common motion tracking location, in accordance with aspects of the present technique.

FIG. 3 illustrates a flow chart 300 depicting an exemplary method for reducing motion artifacts in shear wave measurements. The exemplary method may be described in a general context of computer executable instructions on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 3, the exemplary method is illustrated as a collection of blocks in a logical flow chart, which represents operations that may be implemented in hardware, software, or combinations thereof. The various operations are depicted in the blocks to illustrate the functions that are performed generally during the acquisition and processing of ultrasound data. In the context of software, the blocks represent computer instructions that, when executed by one or more processing subsystems, perform the recited operations. The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIG. 1.

Generally, shear wave imaging is used to generate 2D or 3D images for various diagnostic and/or prognostic purposes. Particularly, shear wave imaging allows differentiation between healthy and diseased tissues based on an estimated velocity of a shear wave as it propagates through designated target locations. Shear wave velocity, in turn, depends on material properties such as varying tissue density and shear modulus. Further, shear wave velocity is often determined using the displacements detected at various target locations. By way of example, the target locations include tissue regions that may have increased or decreased stiffness relative to the average surrounding tissue when afflicted with tumors, cancer and/or hardened blood vessels. Presence of common background motion while tracking these target locations may distort the shear wave measurements leading to incorrect diagnosis.

Accordingly, the ultrasound system 100 employs the present methods to acquire additional data for use in mitigating the corrupting effects of common background motion present during ultrasound imaging using a common motion tracking location. In one embodiment, for example, the term "common motion tracking location" (common location) corresponds to a designated reference location in the target biological tissues.

Accordingly, at steps 302, the ultrasound system 100 begins processing by initializing a location index "i" to a value "0" corresponding to a first target location in a particular frame corresponding to an ROI in target biological tissues. Further, at step 304, the transmit circuitry 102 delivers one or more reference pulses to the common location to determine an initial or default position of the common location. At step 306, the transmit circuitry 102 delivers one or more reference pulses to a plurality of target locations to determine corresponding initial or default positions of the target locations. By way of example, the plurality of target locations corresponds to a plurality of lateral spatial locations corresponding to the target tissues. In certain embodiments, however, the plurality of target locations corresponds to a plurality of depths at a particular lateral and elevational location, a plurality of elevational spatial locations, and/or a plurality of lateral spatial locations on the target tissue.

At step 308, the transmit circuitry 102 and/or the shear wave generator 118 generates a shear wave in the region of interest in the target tissues, for example, using mechanical, electromagnetic and/or acoustic means. Particularly, in one embodiment, the shear wave generator 118 employs acoustic radiation to deliver a pushing pulse at a particular location within the ROI. In an alternative embodiment, however, the point of delivery of the pushing pulse may be outside the ROI. Furthermore, in certain embodiments, the processing unit 114 customizes one or more parameters of the pushing pulse such as frequency, amplitude, and/or pulse length according to imaging requirements. By way of example, the processing unit 114 adjusts acoustic power of the pushing pulse in view of a heating limitation associated with a particular target region. The shear wave travels through the target tissue and causes varying amounts of displacements at different locations in the target tissue.

The processing unit 114 then tracks the displacements caused by the shear wave at the target locations in the ROI. To that end, at step 310, the processing unit 114 initializes a tracking count variable "n" with a zero value. Next, the processing unit 114, at step 312, determines if the tracking counter variable "n" is less than a designated number of tracking pulse firings, "N" for the particular target location. If the tracking count variable "n" is less that the tracking firings "N", at steps 314 and 316, the processing unit 114 directs the transmit circuitry 102 to deliver one or more tracking pulses at the common location and the target location "i" to detect corresponding displacements caused by the shear wave. To that end, the tracking pulses may be delivered to the common location and the target location "i" simultaneously or proximate in time. In certain embodiments, however, the tracking pulses may be delivered to the common location and the target location "i" at substantially different times and may later be interpolated to a common time during processing.

The embodiment illustrated in FIG. 3 depicts steps 304 and 306 corresponding to reference pulse firings before the steps 308-316 corresponding to generating the shear wave and tracking corresponding displacements. In an alternative embodiment, however, the one or more reference pulses may be delivered to the common location and the target location after the displacements caused by the shear wave have been tracked and the target tissue is considered to have returned to a resting or equilibrium position.

Further, at step 318, the processing unit 114 increments the tracking count variable "n" by a value "1" and the method returns control to the step 312. If at step 312, it is determined that the tracking count variable is less than the number of tracking firings "N", the processing unit 114 increments the location index "i" by a value "1" representative of a next target location to be processed at step 320. Further, at step 322, the processing unit 114 determines if the location index "i" is less than a total number of target locations, "M," being tracked by the ultrasound system 100. If the location index "i" is less than a total number of target locations "M," the method returns control to step 304 for determining default/initial positions of the common location and the next target location. The method, thus, acquires data for each of a desired number of target locations by delivering reference pulses, shear wave generating pulses and tracking pulses to the common location and corresponding target locations as discussed herein with reference to steps 304-322.

However, if the location index "i" is greater than the total number of target locations "M" at step 322, the processing unit 114 ascertains that all the locations within the current frame have been processed. Accordingly, the processing unit 114 finishes processing the current frame at step 324. Alternatively, the processing unit 114 determines if a portion or the current frame needs to be processed again at step 326. Accordingly, the processing unit 114 returns the control to step 302 and repeats the data acquisition process for the current frame or terminates the processing of the current frame at step 328. In certain embodiments, the processing unit 114 may also terminate the processing of the current frame, for example, upon receiving user requests to change modes or parameters, on detecting a misplaced positioning of the probe 108 or inappropriate temperature and/or based on image or data derived metrics and return control to step 302.

Figure 4:
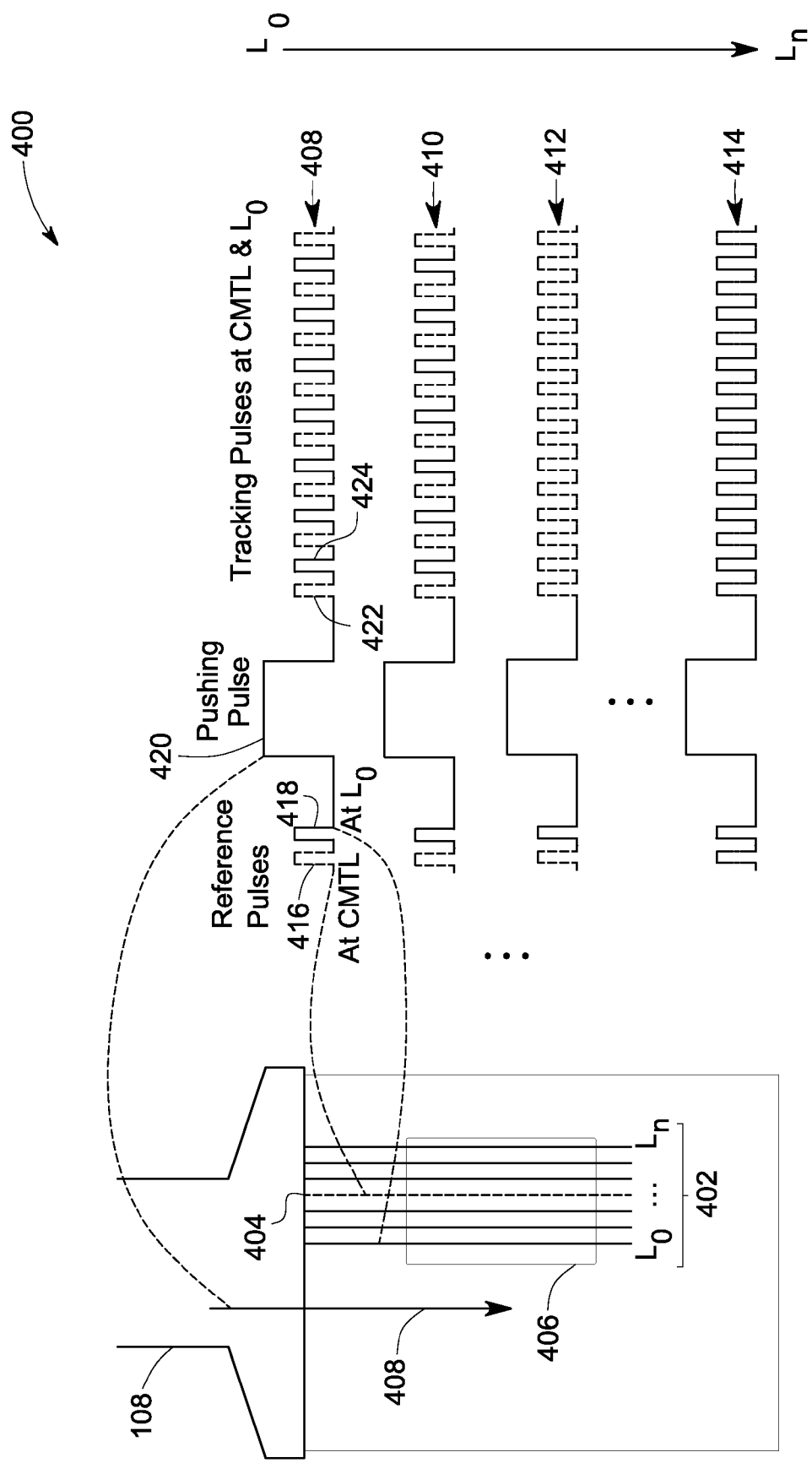
FIG. 4 is a schematic representation of an exemplary scan sequence for measuring shear wave displacements at a plurality of target locations using a common motion tracking location, in accordance with aspects of the present technique.

FIG. 4 illustrates a schematic representation 400 of exemplary scan sequences used in the method illustrated in FIG. 3 for measuring shear wave displacements at a plurality of target locations 402 using a common motion tracking location 404. As previously noted with reference to FIG. 3, the ultrasound probe 108 begins data acquisition for a particular frame corresponding to the ROI 406 in the target tissues.

Particularly, FIG. 4 illustrates exemplary pulse sequences 408, 410, 412 and 414 delivered to the target locations $L_0$, $L_1$, common location 404 and $L_n$, respectively. By way of example, the ultrasound probe 126 delivers the pulse sequence 408 to determine displacements at the first location $L_0$. The pulse sequence 408 includes one or more reference pulses 416, 418 delivered to the common location 404 and the first target location $L_0$, respectively to determine corresponding initial/default positions. To that end, the ultrasound probe 108 delivers the reference pulses 416, 418 to the common location and the target location $L_0$ simultaneously or in an interleaving manner.

The ultrasound probe 108 then generates a shear wave in the ROI 406 of the target tissues, for example, by delivering a pushing pulse 420 at a particular location in the target tissues. The particular location of the delivery of the pushing pulse 420 may be proximate the target location $L_0$ or may be selected such that the generated shear wave causes a detectable level of displacement at the common location 404 and the target location $L_0$.

Further, the ultrasound probe 108 delivers one or more tracking pulses 422, 424 to the common location and the target location to determine corresponding displacements caused by the shear wave traversing through the target tissue. Here again, the ultrasound probe 108 delivers the tracking pulses 422, 424 to the common location and the target location $L_0$ simultaneously or in an interleaving manner, particularly to detect any axial motion experienced at the common location and/or the target location $L_0$. In certain embodiments, however, the ultrasound system 100 employs steered beams or other suitable techniques for detecting lateral motion. Further, the ultrasound probe 126 delivers the pulse sequences, such as 410, 412 and 414 including one or more reference pulses, pushing pulses and tracking pulses to other target locations $L_1$-$L_n$ and the common location 404 in the ROI 406 to acquire corresponding displacement data.

Presence of common motion such as movement of the probe, patient and/or the room during ultrasound imaging, however, may corrupt the displacement measurements detected by the ultrasound system 100 at the common location 404 and the plurality of target locations 402. The corrupted displacement values affect the determination of the tissue characteristics such as stiffness and strain that are indicative of tissue health. Any corruption in the measured displacement values, thus, may lead to an incorrect medical diagnosis. Accordingly, the processing unit 114 uses the acquired displacement data corresponding to the common location to mitigate the corrupting influence of any common background motion present during the imaging process.

Figure 5:
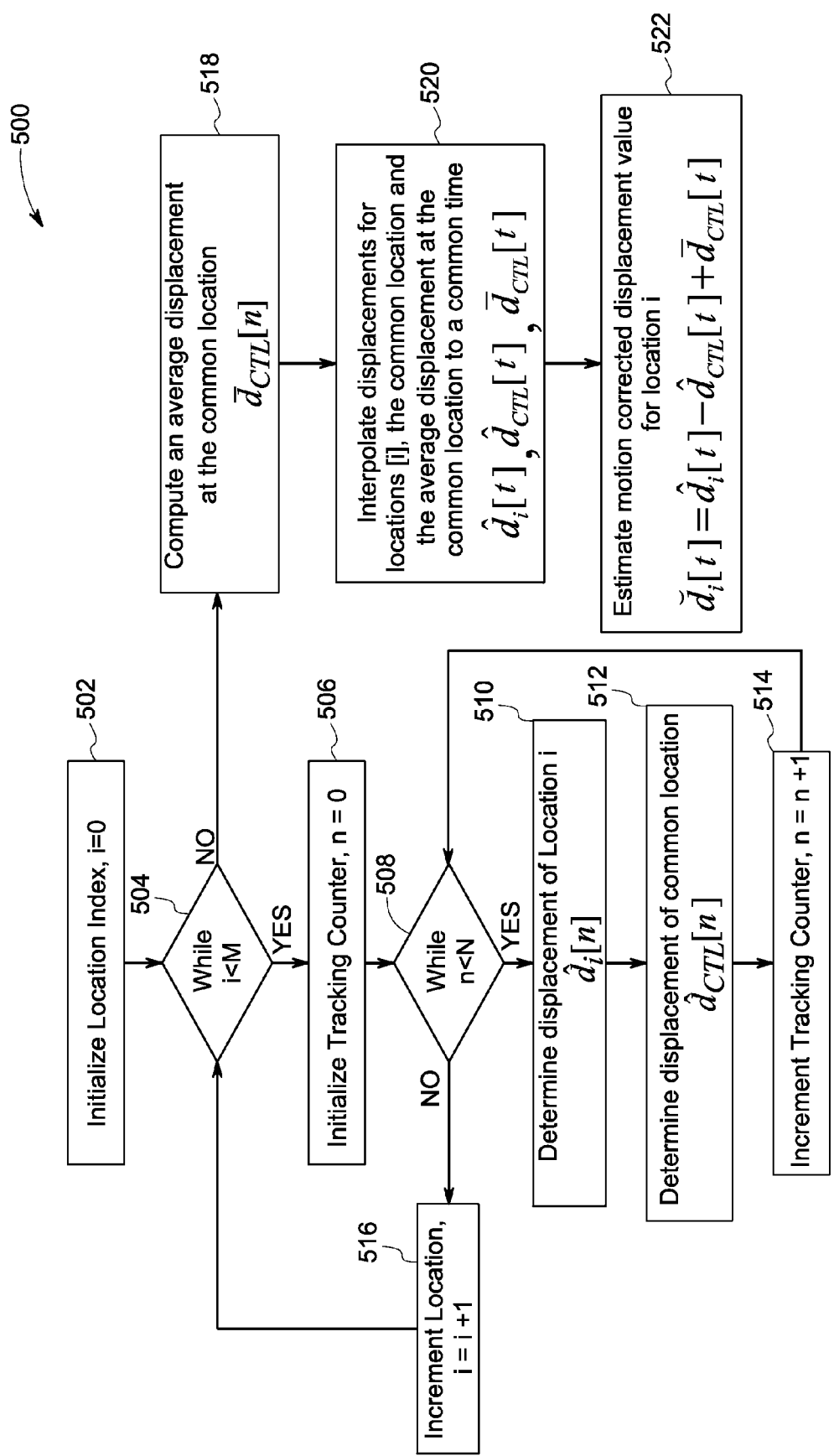
FIG. 5 is a flow diagram illustrating an exemplary method for processing the shear wave displacements acquired using the method of FIG. 3 for estimating motion corrected shear wave displacements at the plurality of target locations, in accordance with aspects of the present technique.

To that end, FIG. 5 illustrates a flowchart 500 depicting an exemplary method of processing the displacement data acquired using the method illustrated in FIG. 3 for estimating motion corrected displacement values for the target locations. Accordingly, the processing unit 114 evaluates data acquired from the plurality of target locations and corresponding displacements detected at the common location to estimate actual displacement of the target locations caused by the shear wave.

To that end, at step 502, the processing unit 114 initializes a location index "i" to a value "0" corresponding to the first target location, for example $L_0$ illustrated in FIG. 4. Next, at step 504, the processing unit 114 determines if the location index "i" is less than a total number of target locations "M," being tracked by the ultrasound system 100. If the location index "i" is less than a total number of target locations "M," the processing unit 114 initializes a tracking count variable "n" with a zero value at step 506. Next, at step 508, the processing unit 114 determines if the tracking counter variable "n" is less than a number of tracking pulse firings, "N" for the particular target location "i."

If the tracking count variable "n" is less that the tracking firings "N", at step 510, the processing unit 114 determines a displacement, $\hat{d}_i[n]$, of the target location "i." In one embodiment, the processing unit 114 determines the displacement detected at the target location "i" based on a difference between the reference and tracking pulse measurements at the target location "i" and time index "n," where the time index "n" corresponds to the different times for which the displacement of the target location "i" is being estimated.

In certain embodiments, for example, the processing unit 114 measures the displacement of a specific target location using a cross-correlation with the reference pulse or a tracking pulse. In alternative embodiments, however, the processing unit 114 may use methods other than cross-correlation, such as, a sum of absolute differences, zero crossing techniques, a sum of the square error, least squares estimation, or other suitable motion estimation techniques. In one embodiment, for example, the displacement measured at the target location "i" may be represented using equation 1 presented herein.

$$\hat{d}_L(t) = d_L(t) + G(t), t = [1, 3, 5, 7 \ldots ]\Delta \qquad \text{(Equation 1)}$$

In Equation 1, the term $\hat{d}_L(t)$ corresponds to the displacements measured at the target location "i," while $d_L(t)$ is the actual displacement at the target location "i" in absence of the common background motion $G(t)$.

Similarly, at step 512, the processing unit 114 determines a displacement, $\hat{d}_{CTL}[n]$ of the common location based on a difference between the reference and tracking pulse measurements at the common location and time index "n." It may be noted that displacement of the common location may be determined at the same time as the displacement at the target location "i," or at a different time. The displacement measured at the common location, for example, may be represented using Equation 2 presented herein.

$$\hat{d}_{CTL}(t+\Delta) = d_{CTL}(t+\Delta) + G(t+\Delta) \qquad \text{(Equation 2)}$$

In Equation 2, the term $\hat{d}_{CTL}(t+\Delta)$ corresponds to the displacements measured at the common location including the common motion displacement, while $d_{CTL}(t+\Delta)$ corresponds to the actual displacement at the common location caused by the shear wave.

Next, at step 514, the processing unit 114 increments the tracking count variable "n" by a value "1" and the method returns control to the step 508. If at step 508, it is determined that the tracking count variable is less than the number of tracking firings "N", the processing unit 114 determines one or more displacement values corresponding to the displacements of the target location "i" and the common location detected by the remaining tracking firings.

Once the value of tracking count variable "n" equals the designated number of tracking firings "N" for the target location "i", at step 516, the processing unit 114 increments the location index "i" by a value "1" representative of a next target location to be processed and returns control to step 504. If the new location index "i" is less than a total number of target locations "M," the processing unit 114 performs steps 506-516 to determine displacements at the new target location "i" and the common location. The method, thus, determines displacement values for the remaining locations "i" in the plurality of target locations "M" and corresponding common location measurements.

However, if the location index "i" is greater than the total number of target locations "M" at step 504, the processing unit 114 ascertains that all the locations within the current frame have been processed. Accordingly, at step 518, the processing unit 114 determines an average value of displacement detected at the common location $\bar{d}_{CTL}[n]$. In one embodiment, for example, the processing unit 114 calculates an average displacement at the common location as the mean or the median of the displacements measured proximate in time to each of the firings corresponding to the "M" locations.

Alternatively, in certain embodiments, the processing unit 114 computes the average displacement of the common location as the mean of RF data or IQ data measured proximate in time to each of the corresponding firings at the "M" locations. Here, the IQ data corresponds to the complex analytic or the complex baseband version of the reference and tracking signals. Further, the processing unit 114 performs cross-correlation of the averaged RF or IQ data for the reference signals and the averaged RF or IQ data for the tracking signals to determine the shear wave induced displacement of the common location. Averaging the data or displacements detected at the common location over multiple firings typically reduces the common background motion component, while retaining the shear wave induced displacement component at the common location.

Similarly, the samples acquired from the plurality of target locations include the displacement caused by the common background motion in addition to the displacement caused by the shear wave traversing through the ROI. Typically, the common background motion is substantially the same at different locations in the target tissues during a particular time. Accordingly, the processing unit 114 processes the acquired samples for eliminating value of the displacement caused due to the common background motion from the displacement detected at the target location "i."

However, there may be a time lag between the delivery of the tracking pulses to the target location "i" and the common location. Accordingly, at step 520, the processing unit 114 interpolates the measured displacements for the target location "i" and the common location to a common time. As used herein, the term "common time" corresponds to substantially the same instant of time. Since the common motion is a function of time, interpolating the displacements at the target location "i" and the common location to the common time allows for an improved removal of the common motion. Accordingly, in one embodiment, the processing unit 114 uses an exemplary linear interpolation depicted in the following Equation 3 to obtain a common time sample "t." Alternative embodiments, however, may employ higher order interpolations and/or sophisticated filtering techniques.

$$\hat{d}_{CTL}(t) = \frac{\hat{d}_{CTL}(t-\Delta) + \hat{d}_{CTL}(t+\Delta)}{2} \quad \text{(Equation 3)}$$

In certain other embodiments, however, instead of interpolating the displacement values to the common time, the processing unit 114 identifies displacement values of the target locations "i" and the common location measured proximate in time.

Next, at step 522, the processing unit 114 estimates a motion corrected displacement for the target location "i." To that end, in one embodiment, the processing unit 114 subtracts the displacement detected at the common location from the displacement detected at the target location "i." Alternatively, the processing unit 114 subtracts the interpolated displacement of the common location (for example, illustrated in equation 3) from the interpolated displacement of the target location "i" (for example, illustrated in equation 1). The subtraction operation substantially cancels out the displacement due to the common motion, while retaining the value of displacement caused by the shear wave motion. Equation 4 illustrates the exemplary subtraction operation performed by the processing unit 114 to eliminate the common background motion component G(t).

$$\hat{d}_L(t) - \hat{d}_{CTL}(t) = d_L(t) + G(t) - (d_{CTL}(t) + G(t)) = d_L(t) - d_{CTL}(t) \quad \text{(Equation 4)}$$

Furthermore, the processing unit 114 adds the average displacement of the common location $\bar{d}_{CTL}[k]$ computed at step 518 to the difference to obtain an estimate of the motion corrected displacement for the target location "i." The motion corrected displacement value for the target location "i," for example, may be represented using the following equation 5.

$$d_L(t) = \hat{d}_L(t) - \hat{d}_{CTL}(t) + \bar{d}_{CTL}(t) \quad \text{(Equation 5)}$$

The motion corrected displacement for the target location "i," thus, is devoid of the corrupting effects of the common background motion component G(t). Accordingly, estimating the motion corrected displacement values by sampling the common location in between sampling the target locations allows for a more accurate assessment of the target tissue characteristics that may be indicative of the nature and extent of specific medical conditions. The accurately assessed tissue characteristics, in turn, aid a medical practitioner in providing an informed medical diagnosis for treating the specific medical conditions.

In certain other embodiments, however, the ultrasound system 100 employs an alternative method for acquiring and processing data from a set of target locations instead of using a common location for estimating corresponding motion corrected displacement values. To that end, FIGS. 6-8 describe an exemplary method that processes data acquired from sets of target locations for estimating motion corrected shear displacement values in greater detail.

Particularly, FIG. 6 illustrates a flow chart 600 depicting an exemplary method for acquiring data from a set of target locations for use in reducing motion artifacts in shear wave measurements. To that end, the present method delivers two or more groups of shear wave scan sequences to each set of target locations. The shear wave scan sequences, for example, include a group of ultrasound reference, pushing, and tracking firings delivered to an ROI in the target tissues for generating a shear wave and tracking displacements caused by the propagation of the shear wave in the ROI of a subject.

Accordingly, at step 602, the processing unit 114 initializes a location index "i" to a value "0" corresponding to a first set of two or more target locations in a particular frame corresponding to an ROI of the target tissues. At step 604, the processing unit 114 ascertains if the location index "i" is less than the total number of target locations "M" being tracked. If the location index "i" is less than "M−1," the processing unit 114 initializes another index "j" corresponding to another target location in the first set of target locations to "i"+1, the target location "j" being common to a second set of target locations. However, if "i" is equal to "M−1," the processing unit 114 initializes the location index "j" to a value "0." In one embodiment, the location "j" is representative of a target location adjacent to the target location "i." In other exemplary implementations, however, the target locations "i" and "j" may correspond to target locations in any designated ordering or in random order in the ROI of the target tissues.

Although FIG. 6 describes the present method using a pair of target locations, certain other embodiments may process sets of two or more target locations in groups to cancel out or at least substantially reduce the corrupting effects of the common background motion from the displacement measurements.

Further, at step 606, the transmit circuitry 102 delivers one or more reference pulses to the set of target locations "i" and "j" to determine corresponding initial, reference or default positions. At step 608, the transmit circuitry 102 and/or the shear wave generator 118 generate a shear wave in the ROI of the target tissues, for example, using mechanical, electromagnetic and/or acoustic means. Particularly, in one embodiment, the shear wave generator 118 employs acoustic radiation to deliver a pushing pulse at a particular location within or outside the ROI. The generated shear wave travels through the target tissues and causes varying amounts of displacements at different locations in the target tissue.

The processing unit 114 then tracks the displacements caused by the shear wave at the target locations in the ROI. To that end, at step 610, the processing unit 114 initializes a tracking count variable "n" with a zero value. Next, the processing unit 114, at step 612, determines if the tracking counter variable "n" is less than a designated number of tracking pulse firings, "N" for the particular set of target locations "i" and "j." If the tracking count variable "n" is less that the tracking firings "N", at step 614, the processing unit 114 directs the transmit circuitry 102 to deliver one or more tracking pulses to the set of target locations "i" and "j" to detect corresponding displacements caused by the shear wave. To that end, the tracking pulses may be delivered to the target locations "i" and "j" simultaneously or at different times.

Additionally, at step 616, the processing unit 114 increments the tracking count variable "n" by a value "1" and the processing unit 114 returns control to the step 612. If at step 612, it is determined that the tracking count variable is less than the number of tracking firings "N", the processing unit 114 increments the location index "i" by a value "1" representative of a next target location to be processed at step 618. Further, at step 620, the processing unit 114 determines if the location index "i" is less than a total number of target locations, "M," being tracked by the ultrasound system 100. If the location index "i" is less than a total number of target locations "M," the processing unit 114 returns control to step 606 for determining default/initial positions of the target locations "i" and "j." The method, thus, acquires data for each of a desired number of target locations by delivering reference pulses, shear wave generating pulses and tracking pulses to the remaining target locations "i" and "j" as discussed herein with reference to steps 606-620.

However, if the location index "i" is greater than the total number of target locations "M" at step 620, the processing unit 114 ascertains that all the locations within the current frame have been processed. Accordingly, the processing unit 114 finishes processing the current frame at step 622. Alternatively, the processing unit 114 determines if a portion or the current frame needs to be processed again at step 624. Accordingly, the processing unit 114 either returns the control to step 602 and repeats the data acquisition process for the current frame or terminates the processing of the current frame at step 626. As previously noted, the processing unit 114 may also terminate the processing of the current frame, for example, based on user requests, probe misplacement, inappropriate temperature and/or image or data derived metrics.

Figure 7:
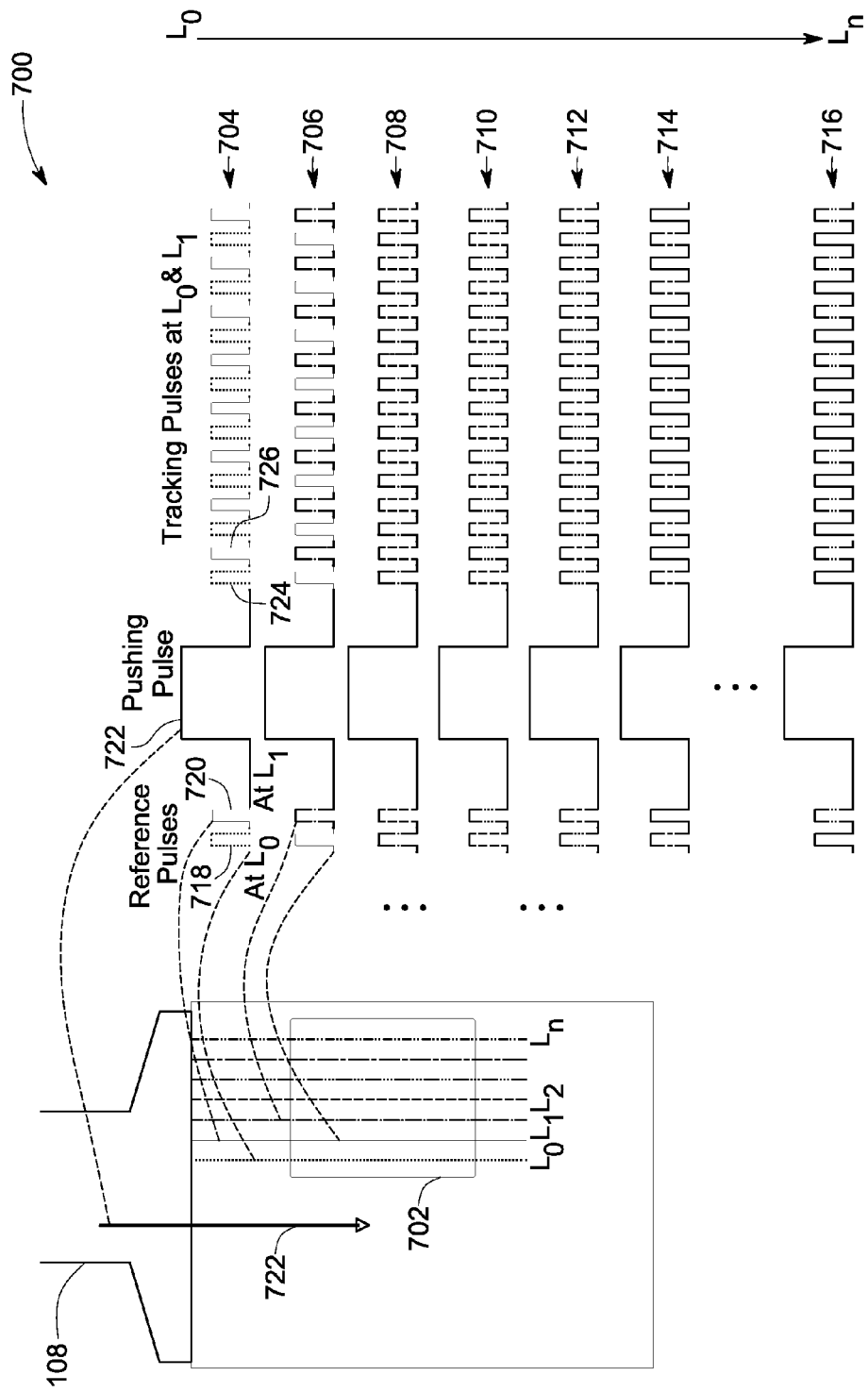
FIG. 7 is a schematic representation of an exemplary scan sequence for measuring shear wave displacements at a plurality of target locations using pairs of tracking locations, in accordance with aspects of the present technique.

FIG. 7 illustrates a schematic representation 700 of exemplary shear wave scan sequences used in the method illustrated in FIG. 6 for measuring shear wave displacements at sets of two or more target locations. As previously noted with reference to FIG. 6, the ultrasound probe 108 begins data acquisition for a particular frame corresponding to the ROI 702 in the target tissues.

Particularly, FIG. 7 illustrates exemplary shear wave scan sequences 704, 706, 708, 710, 712, 714 and 716 delivered to pairs of target locations $L_0$-$L_1$ to $L_{n-1}$-$L_n$. The scan sequence 704, for example, includes reference pulses 718, 720 delivered to the target locations $L_0$ and $L_1$, respectively, to determine corresponding initial/default positions. The ultrasound probe 108 then generates a shear wave in the ROI 702 of the target tissues, for example, by delivering a pushing pulse 722 at a particular location in the target tissues.

Further, the ultrasound probe 108 delivers one or more tracking pulses 724, 726 to a pair of target locations $L_0$-$L_1$ to determine a corresponding displacement caused by the shear wave traversing through the target tissue. Here again, the ultrasound probe 108 delivers the tracking pulses 724, 726 to the target locations $L_0$-$L_1$ simultaneously or in an interleaving manner, particularly to detect any axial motion experienced at the target locations $L_0$-$L_1$. Similarly, the ultrasound probe 126 delivers the other scan sequences 706-716 including one or more reference pulses, pushing pulses and tracking pulses to other pairs of target locations $L_1$-$L_2$ to $L_{n-1}$-$L_n$ to acquire corresponding displacement data.

As previously noted, the patient's breathing or other common background motion may corrupt the displacement measurements acquired from the scan sequences 704-716. Accordingly, the processing unit 114 processes the acquired displacement data from pairs of target locations to mitigate the corrupting influence of common background motion present during the imaging process. To that end, FIG. 8 illustrates a flowchart 800 depicting an exemplary method of processing the displacement data acquired using the method illustrated in FIG. 6 for estimating motion corrected displacement values. Particularly, the processing unit 114 evaluates data acquired from pairs of target locations to estimate actual displacement of the target locations caused by the shear wave.

Accordingly, at step 802, the processing unit 114 initializes a location index "i" to a value zero corresponding to the first target location, for example $L_0$ illustrated in FIG. 7. Next, at step 804, the processing unit 114 determines if the location index "i" is less than a total number of target locations "M," being tracked by the ultrasound system 100. If the location index "i" is less than "M−1," at step 806, the processing unit initializes another index "j" corresponding to another location in the set of target locations to "i"+1, the target location "j" being common to a second set of target locations. However, if "i" is equal to "M−1," the processing unit 114 initializes the location index "j" to a value "0." As previously noted, the target locations "i" and "j" may be located adjacent to each other, in random order or any designated spatial order in the ROI. Next, at step 808, the processing unit 114 initializes a tracking count variable "n" with a zero value. Next, at step 810, the processing unit 114 determines if the tracking counter variable "n" is less than a number of tracking pulse firings, "N" for the particular target location "i."

If the tracking count variable "n" is less that the tracking firings "N", at steps 812, the processing unit 114 determines a displacement, $\hat{d}_i[n]$, of the target location "i." In one embodiment, the processing unit 114 determines the displacement detected at the target location "i" based on a difference between the reference and tracking pulse measurements at the target location "i" and time index "n." where the time index "n" corresponds to the different times for which the displacement of the target location "i" is being estimated. Similarly, at step 814, the processing unit 114 determines a displacement, $\hat{p}_i[n]$ of the target location "j" based on a difference between the reference and tracking pulse measurements at the target location "j" and time index "n." It may be noted that the displacement of the target location "j" may be determined at the same time as the displacement of the target location "i" or at a different time.

Next, at step 816, the processing unit 114 increments the tracking count variable "n" by a value "1" and the method returns control to the step 810. If at step 810, it is determined that the tracking count variable is less than the number of tracking firings "N," the processing unit 114 determines one or more displacement values corresponding to the displacements of the target locations "i" and "j" detected by the remaining tracking firings.

Once the value of tracking count variable "n" equals the number of tracking firings "N", at step 818, the processing unit 114 increments the location index "i" by a value "1" representative of a next target location to be processed and returns control to step 804. If the new location index "i" is less than a total number of target locations "M," the processing unit 114 performs steps 506-818 to determine displacements at another set of target locations "i" and "j." The method, thus, iteratively determines displacement values for the remaining sets of target locations "i" and "j" in the plurality of target locations "M." However, if the location index "i" is greater than the total number of target locations "M" at step 804, the processing unit 114 ascertains that all the locations within the current frame have been processed.

The samples acquired from the different target locations include the displacement caused by the common background motion in addition to the displacement caused by the shear wave traversing through the ROI. Typically, the common background motion is substantially the same at different locations in the target tissues during a particular time. However, there may be a time lag between the delivery of the tracking pulses to the target locations "i" and "j."

Accordingly, at step 820, the processing unit 114 interpolates the determined displacements for the target location "i" and "j" at a common time. The common time, for example, corresponds to either substantially the same instant of time or a designated period of time. As previously noted, the common motion is a function of time. Accordingly, interpolating the displacements of the target locations "i" and "j" to the common time allows for an improved removal of the common motion. In one embodiment, for example, the processing unit 114 uses one or more of linear or higher order interpolations and/or sophisticated filtering techniques to obtain displacement values corresponding to, $\hat{d}_i[t]$ and $\hat{p}_i[t]$, at a common time sample "t." However, in certain embodiments, instead of interpolating the displacement values to the common time, the processing unit 114 identifies displacement values of the target locations "i" and "j" measured proximate in time.

Next, at step 822, the processing unit 114 computes a difference between the displacements of each pair of target locations "i" and "j" measured proximate in time. Alternatively, the processing unit 114 computes a difference $\check{\Delta}_i[t]$ between the interpolated displacements of each pair of the target locations "i" and "j," for example, as illustrated in Equation 6 where "i" varies from 1 to M−1. The subtraction operation substantially cancels out the displacement owing to the common motion, while retaining the value of displacement caused by the difference in the shear wave motion at the two locations.

$$\check{\Delta}_i[t] = \hat{d}_i[t] - \hat{p}_i[t] \quad \text{(Equation 6)}$$

Further, the processing unit 114, at step 824, estimates a motion corrected displacement $\check{d}_0[t]$ for the first target location "i=0." To that end, in one embodiment, the processing unit 114 estimates a seed value for estimating the motion corrected displacement $\check{d}_0[t]$ for the first target location "i=0." The seed value, for example, is estimated as the measured and interpolated displacement value as in Equation 7.

$$\check{d}_0[t] = \hat{d}_0[t] \quad \text{(Equation 7)}$$

In an embodiment where the seed value is estimated as illustrated in Equation 7, the motion corrected displacement estimates may still contain a common background motion component. Although this common motion component may introduce a constant offset error in the image, the component will be the same for the entire image, thus, greatly reducing the appearance of striped artifacts in the image. In an alternative embodiment, however, the seed value is estimated from a separate set of firings at the target location "i" that is repeated to average out the background motion.

Next, at step 826, the processing unit 114 initializes location index "i" to "1" for processing the remaining target locations. The processing unit 114 ascertains if the location index "i" is less than the total number of target locations "M" being tracked. If the location index "i" is less than "M," the processing unit 114 estimates motion corrected displacements of the next target location in the remaining target locations in the first set at step 830. To that end, the processing unit 114 computes a difference between the estimated seed value and the corresponding difference computed at step 824. Equation 8 illustrates the exemplary operation performed by the processing unit 114 to estimate a motion corrected displacement of each of the remaining target locations in the first set of target locations.

$$\check{d}_i[t] = \check{d}_{i-1}[t] - \check{\Delta}_i[t] \quad \text{(Equation 8)}$$

To that end, at step 832, the location index "i" is incremented by one to estimate the motion corrected displacement values for each of the remaining target locations. In one embodiment, the processing unit 114 estimates motion corrected displacements for the second set of target locations using motion corrected displacements estimated for the target locations that are common to the first and second sets of target locations and the corresponding computed difference.

Processing actual displacements detected at pairs of locations to cancel the corrupting effects of the common background motion component substantially improves the quality of the corresponding ultrasound images. The high quality images, in turn, allow for a more accurate assessment of the target tissue characteristics indicative of the nature and extent of specific medical conditions. FIG. 9, for example, illustrates an ultrasound image 902 including striped artifacts owing to the corrupting influence of the common background motion.

Typically, the striped noise pattern changes as a function of time and varies across the different tracking pulses because the ultrasound system 100 collects tracking pulses at different times.

Certain shear wave imaging techniques employ custom-designed filters to mitigate appearance of such striped noise patterns in the ultrasound images. These filters are not always effective or efficient in removing background motion artifacts from shear wave images. However, the present methods, such as described in FIGS. 3-8, allow canceling the common motion from the shear wave measurements to allow generation of good quality ultrasound images, such as the image 904 illustrated in FIG. 9. More particularly, the present methods describe acquiring and processing data from a common location or a pair of target locations interpolated to a common time to average out the common motion from measured displacement values. The present methods, thus, reduce motion artifacts such as striped noise patterns to allow for generation of ultrasound images that aid in accurate diagnosis of medical conditions.

The exemplary embodiments of the systems and methods disclosed hereinabove describe the use of a common location or pairs of target to provide motion corrected shear displacement estimations. The motion corrected displacement values may then be used to generate high resolution ultrasound images that provide greater detail and reliable information regarding tissue characteristics to aid in a substantially accurate diagnosis.

The present systems and methods, thus, may be employed to generate ultrasound images that aid in assessing mechanical properties of tissues or any other material that is suitable for ultrasound imaging. By way of example, the systems and methods facilitate a more accurate assessment of arterial stiffness, muscle tone and kidney stiffness for distinguishing between healthy and diseased tissues based on an improved estimate of shear wave displacements. Additionally, the exemplary shear wave imaging methods may also be used in radio frequency (RF) ablation therapy such as used for liver cancer for monitoring the progress of the therapy in near real-time.

Furthermore, the foregoing examples, demonstrations, and process steps such as those that may be performed by the processing unit 114 and shear wave generator 118 may be implemented by suitable code on a processor-based system, such as a general-purpose or special-purpose computer. It should also be noted that different implementations of the present technique may perform some or all of the steps described herein in different orders or substantially concurrently, that is, in parallel. In addition, the functions may be implemented in a variety of programming languages, including but not limited to Python, C++ or Java. Such code may be stored or adapted for storage on one or more tangible, machine readable media, such as on data repository chips, local or remote hard disks, optical disks (that is, CDs or DVDs), or other media, which may be accessed by a processor-based system to execute the stored code.

While only certain features of the present invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for reducing motion artifacts in shear wave measurements, comprising:
   delivering one or more reference pulses to a common motion tracking location and to a plurality of target locations in a region of interest to detect initial positions of the common motion tracking location and the plurality of target locations;
   generating a shear wave in the region of interest;
   delivering one or more tracking pulses to the common motion tracking location and to the plurality of target locations for determining displacements of the common motion tracking location and the plurality of target locations;
   computing an average value of displacement of the common motion tracking location; and
   estimating a motion corrected displacement for a target location in the plurality of target locations based on a displacement of the target location at a particular time, the corresponding displacement of the common tracking location measured proximate in time to the measurement of the displacement of the target location and the average value of displacement of the common motion tracking location.

2. The method of claim 1, further comprising interpolating the displacement of the plurality of target locations and a corresponding displacement of the common motion tracking location to a common time.

3. The method of claim 2, wherein estimating a motion corrected displacement for the plurality of target locations comprises:
   computing a difference between the displacement of the common tracking location interpolated to the common time from the displacement of the corresponding target location interpolated to the common time, and
   adding the average value of displacement of the common motion tracking location to the computed difference to generate an estimate of the motion corrected displacement of the corresponding target location.

4. The method of claim 1, wherein the motion corrected displacement value is used to determine strain of a target tissue, shear modulus of the target tissue, Young's modulus of the target tissue, viscosity of the target tissue, to generate an elasticity image of the target tissue, or combinations thereof.

5. The method of claim 1, wherein the one or more reference pulses are delivered to the common motion tracking location and the plurality of target locations to detect corresponding initial positions after delivering the one or more tracking pulses to the common motion tracking location and the plurality of target locations.

6. The method of claim 1, wherein the one or more reference pulses are delivered to the common motion tracking location and the plurality of target locations to detect corresponding initial positions before generating the shear wave in the region of interest.

7. The method of claim 1, wherein generating the shear wave comprises applying acoustic radiation force within or proximate the region of interest.

8. The method of claim 1, wherein generating the shear wave comprises applying mechanical force within or proximate the region of interest.

9. The method of claim 1, wherein generating the shear wave comprises applying electromagnetic force within or proximate the region of interest.

10. The method of claim 1, wherein delivering the one or more tracking pulses comprises delivering the one or more tracking pulses to the common motion tracking location and each of the plurality of target locations simultaneously or in an interleaving manner.

11. The method of claim 1, wherein determining the displacements of the common motion tracking location and each of the plurality of target locations comprises using speckle tracking, a sum of absolute differences, an iterative phase zeroing technique, a direct strain estimation, a cross-correlation, an auto-correlation, or combinations thereof.

12. The method of claim 1, wherein the plurality of target locations comprise one or more of a biological tissue and a compressible portion of an object for industrial inspection.

13. A method for reducing motion artifacts in shear wave measurements, comprising:
 delivering at least two groups of shear wave scan sequences, each group comprising:
  delivering one or more reference pulses to a first set of target locations in a region of interest to detect corresponding initial positions, wherein at least one of the first set of target locations is common to a second set of target locations;
  generating a shear wave in the region of interest;
  delivering one or more tracking pulses to the first set of target locations for determining corresponding displacements; and
  computing displacements for the first set of target locations based on measurements captured using the one or more reference pulses and the one or more tracking pulses delivered to the corresponding target locations in the first set of target locations;
 for each group of shear wave scan sequences:
  interpolating the determined displacements for the first set of target locations and the second set of target locations to a common time;
   computing a difference between the interpolated displacement of a target location in the first set of target locations and the interpolated displacement of another target location in the first set of target locations;
   estimating a seed value using the measured and interpolated displacements from the target location in the first set of target locations;
   estimating motion corrected displacements for other target locations in the first set of target locations based on the estimated seed value and the computed difference between interpolated displacement of the target location and the interpolated displacement of another target location in the first set of target locations; and
   estimating motion corrected displacements for the second set of target locations using the computed difference and the motion corrected displacements estimated for target locations in the first set of target locations that are common to the second set of target locations.

14. The method of claim 13, wherein estimating the seed value comprises using an average value of displacement of the target location determined by repeatedly delivering reference and tracking pulses to the target location for reducing a background motion component of a displacement measured at the target location.

15. The method of claim 13, wherein the one or more reference pulses are delivered to the plurality of target locations to detect corresponding initial positions before generating the shear wave in the region of interest.

16. The method of claim 13, wherein the one or more reference pulses are delivered to the first set of target locations to detect corresponding initial positions after delivering the one or more tracking pulses to the first set of target locations.

17. The method of claim 13, wherein delivering the one or more tracking pulses comprises delivering the one or more tracking pulses to the set of two or more target locations simultaneously or in an interleaving manner.

18. The method of claim 13, wherein the plurality of target locations comprise one or more of a biological tissue and a compressible portion of an object for industrial inspection.

19. A non-transitory computer readable medium that stores instructions executable by one or more processors to perform a method for reducing motion artifacts in shear wave measurements, comprising:
 delivering one or more reference pulses to a common motion tracking location and to a plurality of target locations in a region of interest to detect initial positions of the common motion tracking location and the plurality of target locations;
 generating a shear wave in the region of interest;
 delivering one or more tracking pulses to the common motion tracking location and to the plurality of target locations for determining displacements of the common motion tracking location and the plurality of target locations; and
 computing an average value of displacement of the common motion tracking location;
 estimating a motion corrected displacement for a target location in the plurality of target locations based on a displacement of the target location at a particular time, the corresponding displacement of the common tracking location measured proximate in time to the measurement of the displacement of the target location and the average value of displacement of the common motion tracking location.

20. A non-transitory computer readable medium that stores instructions executable by one or more processors to perform a method for reducing motion artifacts in shear wave measurements, comprising:
 delivering at least two groups of shear wave scan sequences, each group comprising:
  delivering one or more reference pulses to a first set of target locations in a region of interest to detect corresponding initial positions, wherein at least one of the first set of target locations is common to a second set of target locations;
  generating a shear wave in the region of interest;
  delivering one or more tracking pulses to the first set of target locations for determining corresponding displacements; and
  computing displacements for the first set of target locations based on measurements captured using the one or more reference pulses and the one or more tracking pulses delivered to the corresponding target locations in the first set of target locations;
 for each group of shear wave scan sequences:
  interpolating the determined displacements for the first set of target locations and the second set of target locations to a common time;
   computing a difference between the interpolated displacement of a target location in the first set of target locations and the interpolated displacement of another target location in the first set of target locations, wherein the another target location is common to the second set of target locations;
   estimating a seed value using the measured and interpolated displacements from the target location in the first group set of target locations;

estimating motion corrected displacements for other target locations in the first set of target locations based on the estimated seed value and the computed difference between interpolated displacement of the target location and the interpolated displacement of another target location in the first set of target locations; and estimating motion corrected displacements for the second set of target locations using motion corrected displacements estimated for target locations in the first set of target locations that are common to the second set of target locations and the computed difference.

\* \* \* \* \*